(12) United States Patent
Jensen et al.

(10) Patent No.: US 6,265,385 B1
(45) Date of Patent: Jul. 24, 2001

(54) TOPOISOMERASE II POISON AND BIS-DIOXOPIPERAZINE DERIVATIVE COMBINATION THERAPY

(75) Inventors: Peter Buhl Jensen, Farum; Maxwell Sehested, København Ø, both of (DK)

(73) Assignee: Topo Target ApS, Copenhagen (DK)

( * ) Notice: Subject to any disclaimer, the term of this patent is extended or adjusted under 35 U.S.C. 154(b) by 0 days.

(21) Appl. No.: 09/101,499

(22) PCT Filed: Jan. 10, 1997

(86) PCT No.: PCT/DK97/00013

§ 371 Date: Mar. 8, 1999

§ 102(e) Date: Mar. 8, 1999

(87) PCT Pub. No.: WO97/25044

PCT Pub. Date: Jul. 17, 1997

(30) Foreign Application Priority Data

Jan. 11, 1996 (DK) .................................................. 0022/96

(51) Int. Cl.⁷ .................................................. A61K 31/70
(52) U.S. Cl. .............................. 514/34; 514/35; 514/252; 514/255; 536/4.1; 544/357; 544/358
(58) Field of Search ................................ 514/34, 35, 252, 514/255; 536/4.1; 544/357, 358

(56) References Cited

U.S. PATENT DOCUMENTS

| 5,242,901 | 9/1993 | Speyer et al. ............................. 514/8 |
| 5,587,382 | 12/1996 | Krapcho et al. ...................... 514/290 |

FOREIGN PATENT DOCUMENTS

| 2163601 | * 6/1972 | (DE) . |
| 0 393 575 | 10/1990 | (EP) . |
| 0409499 | * 1/1991 | (EP) . |
| 2 257 430 | 1/1993 | (GB) . |
| WO 86/00812 | 2/1986 | (WO) . |
| WO 92/08460 | 5/1992 | (WO) . |
| 9208460 | * 5/1992 | (WO) . |
| 9307873 | * 4/1993 | (WO) . |

OTHER PUBLICATIONS

Hasinoff et al., "Chemical, Biological and Clinical Aspects of Dexrazoxane and Other Bisdioxopiperazines," *Current Medicinal Chemistry*, 5(1), 1–28 (1998).*
Clark et al., "The Clinical Pharmacology of Etoposide and Teniposide," *Clinical Pharmacokinetics*, 12, 223–252 (1987).*
Holm et al., "Improved Targeting of Brain Tumors Using Dexrazone Rescue of Topoisomerase II Combined with Supralethal Doses of Etoposide and Teniposide," *Clinical Cancer Research*, 4, 1367–1373 (Jun., 1998).*
Chabner, "Anticancer Drugs," and Grever et al., "Cancer Drug Discovery and Development," Chapter 18, Introduction and Section 1 in *Cancer: Principles & Practice of*

(List continued on next page.)

Primary Examiner—Gary Geist
Assistant Examiner—L. E. Crane
(74) *Attorney, Agent, or Firm*—Iver P. Cooper

(57) ABSTRACT

The present invention relates to a method for selectively killing tumor or metastatic cells within a defined compartment of the organism of a large mammal, in particular a human, said method comprising administering to a mammal an effective tumor—or metastasis-killing amount of a topoisomerase II poison except doxorubicin, and protecting non-tumorous tissue of the mammal against the toxic action of the topoisomerase II poison by administration of a bis-dioxypiperazine compound. In particular, the invention relates to a pharmaceutical kit for selectively killing tumor or metastatic cells within the central nervous system in a large mammal, in particular a human, said kit comprising: a) a dosage unit of a bis-dioxypiperazine and a pharmaceutically acceptable carrier, and b) a dosage unit of topoisomerase II poisons except doxorubicin and a pharmaceutically acceptable carrier.

54 Claims, 1 Drawing Sheet

OTHER PUBLICATIONS

Oncology, Fourth Edition, De Vita, Jr. et al. (eds.), J. B. Lippincott Co, Philadelphia, PA, 1993, only pp. 325–340 supplied.*

Wasserman et al., "Mechanistic Studies of Amsacrine–resistant Derivatives of DNA Topoisomerase II," *Journal of Biological Chemistry*, 269(33), 20943–20951 (Aug. 19, 1994).*

Von Hoff et al., "Pharmacokinetics of ICRF–187 in the Cerebrospinal Fluid of Subhuman Primates," *Cancer Treatment Reports*, 64(4–5), 734–736 (Apr./May, 1980).*

Ishida et al., "Inhibition of Intracellular Topoisomerase II by Antitumor Bis(2,6–dioxopiperazine) Derivatives: Mode of Cell Growth Inhibition Distinct from that of Cleavable Complex–forming Type Inhibitors," *Cancer Research*, 51, 4909–4916 (Sep. 15, 1991).*

Sehested, Maxwell et al., "Antangonistic effect of the cardioprotector (+)–1,2–bis(3, 5–dioxopiperazinyl–1–yl) propane (icrf–187) on dna breaks and cytotoxicity induced by the topoisomerase II directed drugs daunorubicin and etoposide (vp–16).", Biochemical Pharmacology, vol. 46, No. 3, pp. 389–393 (1993).

Jensen, Peter et al, "Targetting the cytotoxicity of topoisomerase II–directed epipodophyl lotoxins to tumor cells in acidic environments.", Cancer Research, vol. 54, pp. 2959–2963 (Jun. 1, 1994).

Tanabe, Kazushi et al., "Inhibition of topoisomerase II by antitumor agents bis(2,6–dioxopiperazine derivatives.", Cancer Research, vol. 51, pp. 4903–4908 (Sep. 15, 1991).

Herman, Eugene et al., "Biological properties of ICRF–159 and related bis(dioxopiperazine) compounds,", Advances in Pharmacology and Chemotherapy, vol. 19, pp. 249–290 (1982).

Bork et al., "Teniposide and Etoposide in Previously Untreated Small–Cell Lung Cancer: A Randomized Study", J. Clin. Oncology, vol. 9, (Sep. 1991, #9) pp. 1627–1631.

Cornfield et al., "Some New Aspects of the Application of Maximum Likelihood to the Calculation of the Dosage Response Curve", American Statistical Asso. Journal, pp. 181–210 (Jun. 1950).

Dand, "Development of Resistance to Daunomycin (NSC–82151) In Ehrlich Ascites Tumor", Cancer Chemotherapy Reports, Part 1, vol. 55, No. 2, (1971) pp. 133–141 (Apr. 1971).

Donelli, "Do Anticancer Agents Reach the Tumor Target in the Human Brain", Cancer Chemother Pharmacol, vol. 30, (1992) pp. 251–260.

Finlay, "Chemoprotection by 9–Aminoacridine Derivatives Against the Cytotoxicity of Topoisomerase II–Directed Drugs", Eur. J. Cancer Clin. Oncol., vol. 25, No. 12, (1989) pp. 1695–1701.

Holm et al., "In Vivo–Inhib. Etoposide–Mediated Apoptosis, Toxicity, Antitumor Effect by the Topoisomerase II–Uncoupling Anthracycline Aclarubicin", Cancer Chemother Pharmacol, vol. 34, (1994) pp. 503–508.

Jensen et al., "Antitumor Activity of the Two Epipodophyllotoxin Derivatives VP–16 & VM–26 in Preclin. Sys.: A Compar. of In Vitro & In Vivo Drug Evaluation", Cancer chemother Pharmacol, vol. 27, (1990) pp. 194–198.

Jensen et al., "Antag. Effect Aclarubicin on Cytoxicity of Etoposide & 4'–(9–Acridinylamino)Methanesulfon- –m–Anisidide Hum. Sm. Cell Lung Cancer Cell . . . ", Cancer Res., vol. 50, pp. 3311–3316 (Jun. 1, 1990).

Jensen et al., "Antog. Effect of Aclarubicin on Daunorubicin–Induced Cytotox. Hum. Sm. Cell Lung Cancer Cells: Relation. to DNA Integ. & Topoisomerase II", Cancer Res., vol. 51., pp. 5093–5099 (Oct. 1991).

Jensen et al., "Different Modes of Anthracycline Interaction w/Topoisomerase II", Biochemical Pharmacology, vol. 45, No. 10, (1993) pp. 2025–2035.

Liu, "DNA Topoisomerase Poisons as Antitumor Drugs", Ann. Rev. Biochem., vol. 58, (1989) pp. 351–75.

Pommier et al., "Role of DNA Intercalation in the Inhibition of Purified Mouse Leukemia (L1210) DNA Topoisomerase II By 9–Aminoacridines", Biochemcu Pharmacology, vol. 36, No. 20, (1987) pp. 3477–3486.

Pommier et al., "Topoisomerase II Inhibition by Antitumor Intercalators and Demethylepipodophyllotoxins", Developments in Cancer Chemotherapy, vol. II, (1989) pp. 175–195.

Roca, "Antitumor Bisdioxopiperazines Inhibit Yeast DNA Topoisomerase II by Trapping the Enzyme in the Form of a Closed Protein Clamp", Proc. Natl. Acad. Sci., vol. 91, 1781–1785 (Mar., 1994).

Roca et al., "DNA Transport by a Type II DNA Topoisomerase: Evidence n Favor of A Two–Gate Mechanism", Cell, vol. 77, pp. 609–616 (May 20, 1994).

Rowe et al., "Inhibition of Epipodophyllotoxin Cytotoxicity by Interference w/Topoisomerase–Mediated DNA Cleavage", Biochemical Pharmacology, vol. 34, No. 14, (1985) pp. 2483–2487.

Tennery, Adriamycin–Induced DNA Damage Mediated By Mammalian DNA Topoisomerase II, Science, vol. 226 pp. 466–468 (Oct. 26, 1984).

Woodman et al., "Enhancement of the Effectiveness of Daunorubicin (NSC–82151 or Adriamycin NSC–123127) Against Early Mouse L1210 Leukemia with ICRF–159 (NSC–1129943)" vol. 159(4), Cancer Chemo. Rpts. (Jul./Aug. 1975).

Woodman, "Enhanc. of Antitumor Effectiveness of ICRF–159 (NSC–129943) Against Early L1210 Leukemia by Comb. w/Cis–Diamminedichloroplat . . . ", Cancer Chemo. Rpts. Part 2, vol. 4, No. 1 pp. 45–52 (Mar. 1974).

Wheeler et al., "The Cytokinetic and Cytotoxic Effects of ICRF–159 & ICRF–187 in vitro & ICRF–187 in Human Bone Marrow in vivo", Investiga. New Drugs I, (1983) pp. 283–295.

Wang et al., "Reduction of Daunomycin Toxicity by Razoxane", Br. Journal of Cancer, vol. 43, (1981) pp. 871–877.

Walder et al., "Lethal Sublethal Effec. Combin. Doxorubicin Bisdioxopiperazine, (1)–1,2,–Bis(3–5–Dioxop.–1–YL) Propane (ICRF 187), Murine Sarcoma S180 In Vitro", Biochem. Pharm., vol. 36, No. 9, (1987) pp. 1495–1501.

Villani et al., "Effect of ICRF–187 Pretreatment Against Doxorubicin–Induced Delayed Cardiotoxicity in the Rat", Toxicology and Applied Pharmacology, vol. 102, (1990) pp. 292–299.

Sorensen et al., "Cardioprotect. ADR–529 High–Dose Epirubicin Given Combin. Cyclophosphamide, 5–Fluorouracil and Tamoxifen . . . ", Cancer Chemother Pharmacol, vol. 34, (1994) pp. 439–443.

Schurig et al., "The Mouse as a Model for Predicting the Myelosuppressive Effects of Anticancer Drugs", Cancer Chemother Pharmacol, vol. 16, (1986) pp. 243–246.

Greig et al., "Razoxane Penetration into the Cerebrospinal Fluid of Rats", Cancer Chemother Pharmacol, vol. 8, (1982) pp. 251–252.

Hochster et al., "Pharmacokinetics Cardioprotector ADR–529 (ICRF–187) in Escalating Doses Combined w/Fixed–Dose Doxorubicin", vol. 84, No. 22, (1992) pp. 1725–1730 J. Nat. Can. Inst. (Nov. 18, 1992).

Gorbsky, "Cell Cycle Prog. Chromos. Segreg. Mammalian Cell Cultur. Presence Topoisomerase II Inhib . . . " Cancer Research, vol. 54, pp. 1042–1048 (Feb. 15, 1994).

Clarke et al., "Topoisomerase II Inhibition Prevents Anaphase Chromatid Segregation in Mammalian Cells Independently of Genration of DNA Strand Breaks", J. of Cell Sci., vol. 105, (1993) pp. 563–569.

Ishimi et al., "Effect of ICRF–193, a Novel DNA Topoisomerase II Inhibitor, on Simian Virus 40 DNA . . . " Molecular and Cellular Biology, vol. 12, No. 9, pp. 4007–4014 (Sep., 1992).

Ishida et al., "DNA Topoisomerase II is the Molecular Target of Bisdioxopiperazine Derivatives ICRF–159 and ICRF–193 in Saccharomyces Cerevisiae", Cancer Res., vol. 55, pp. 2299–2303 (Jun. 1, 1995).

Baba et al., "Protective Effect of ICRF–187 against Normal Tissue Injury by Adriamycin in Combination with Whole Body Hyperthermia", Cancer Res., vol. 51, pp. 3568–3577 (Jun. 1, 1991).

El–Hage et al., "Mechanism of the Protective Activity of ICRF–187 Against Alloxan–Induced Diabetes in Mice", Research Communications in Chemical Pathology and Pharmacology, vol. 52, No. 3, pp. 341–360 (Jun. 1986).

Fukuda et al., "Effect of ICRF–187 on the Pulmonary Damage Induced by Hyperoxia in the Rat", Toxicology, vol. 74, (1992) pp. 185–202.

Giuliani et al., "Studies in Mice Treated with ICRF–159 Combined with Daunorubicin or Doxorubicin", Cancer Treatment Reports, vol. 65, No. 3-4, pp. 267–276 (Mar./Apr., 1981).

Green et al., "Evidence of the Selective Alteration of Anthracycline Activity Due to Modulation by ICRF–187 (ADR–529)", Pharmac. Ther. vol. 48, (1990) pp. 61–69.

Hellman et al., "Amelioration of Antitumor Drug Toxicity", Cancer Treatment Reviews, vol. 11, (1984) pp. 295–297.

Herman et al., "Modification of Some of the Toxic Effects of Daunemycin/NSC by Pretreatment with Antineoplastic Agent ICRF 159 (NSC–129,943)", Toxicolo. Applied Pharmacol., vol. 27, (1974) pp. 517–526.

Walder et al., "Synergistic Activity of Doxor. and Bisdioxop. (+)–1,2–Bis(3,5–Dioxopip.–1–yl)Propane . . . ", Cancer Research, vol. 46, pp. 1176–1181 (Mar. 1986).

Ishida et al., "Inhibition of Intracellular Topoisomerase II by Antitumor Bis(2,6–Dioxopip.) . . . ", Cancer Research, vol. 51, pp. 4909–4916 (Sep. 15, 1991).

Kano et al., "The Effects of ICRF–154 in Combination with Other Anticancer Agents in Vitro", Br. Journal of Cancer, vol. 66, (1992) pp. 281–286.

Levine et al., "Preclinical Toxicologic Evaluation of ICRF–187 in Dogs", Cancer Treatment Reports, vol. 64, No. 12, pp. 1211–1215 (Dec. 1980).

Lipshultz, "Dexrazoxane for Protection Against Cadiotoxic Effects of Anthracyclines in Children", Journal of Clinical Oncology, vol. 14, No. 2, pp. 328–333 (Feb. 1996).

Speyer et al., "Protective Effect of Bispiperazinedione ICRF–187 Against Doxorubicin–Induced Cardiac Toxicity In Women with Advanced Breast Cancer", New Eng. J. of Med., vol. 319, pp. 745–752 (Sep. 22, 1988).

Speyer et al., "ICRF–187 Permits Longer Treatment with Doxorubicin in Women with Breast Cancer", Journal of Clinical Oncology, vol. 10, No. 1, pp. 117–127 (Jan., 1992).

Sehested et al., "Mapping of DNA Topoisomerase II Poisons (Etoposide, Cloerocidin) and Catalytic Inhibitors . . . ", Biochemical Pharmacology, vol. 51, (1996) pp. 1–8.

* cited by examiner

—— m-AMSA 45 mg/kg
------ m-AMSA 55 mg/kg
——— ICRF-187 125mg/kg + m-AMSA 45 mg/kg
—·—· ICRF-187 125mg/kg + m-AMSA 45 mg/kg

TOPOISOMERASE II POISON AND BIS-DIOXOPIPERAZINE DERIVATIVE COMBINATION THERAPY

This application is the national stage of PCT/DK97/00013, filed Jan. 10, 1997, which is a continuation-in-part of Ser. No. 08/603,105, filed Feb. 20, 1996, now abandoned.

FIELD OF INVENTION

The present invention relates to the treatment of malignant conditions which are sensitive to topoisomerase II poisons. In particular, the invention relates to a method for selectively killing tumour or metastatic cells within the central nervous system of a large mammal such as a human.

BACKGROUND OF THE INVENTION

Studies concerning patients suffering from primary cancer outside the central nervous system (CNS) show that 20–25% of the patients develop metastasis of the CNS. However, the risk of developing metastases is dependent on the specific cancer form.

The metastatic complications are very often the patient's first symptom of cancer and may give rise to serious neurological complications at a time when the patient is unaffected by the primary cancer.

The treatment of primary cancer and metastasis of the CNS is far from satisfactory. Most measures, whether radiotherapy or chemotherapy, are limited by the fact that the treatment also affects the normal tissue; accordingly, the tolerance of the normal tissue to the specific treatment is of great importance. The most serious side-effect of chemotherapy is myelosuppression.

The target site for cytotoxic drugs differs significantly among cancer drugs. The essential nuclear enzyme topoisomerase II allows the separation of intertwined DNA strands by creating a transient double stranded break in the DNA backbone. This catalytic cycle of topoisomerase II is believed to be the target of some of the most successful antitumour agents used today, e.g. etoposide (VP-16) in the treatment of testicular and small cell lung cancer (2). There is solid evidence that etoposide, as well as a number of other clinically successful antitumour agents such as daunorubicin and doxorubicin (Adriamycin) (28), are active by inhibiting the resealing of the DNA breaks created by topoisomerase II (19, 21). Although the precise cell killing mechanism is unknown, an obligatory step for the cytotoxicity of the topoisomerase II targeting agents is an increase in cleavable complexes between DNA and topoisomerase II (19). This complex mechanism of cell killing is susceptible to drug modulation.

The clinically active DNA intercalating drug, aclarubicin, completely antagonizes the cytotoxicity of topoisomerase II targeting agents such as etoposide, teniposide, m-AMSA, (amsakrin; 4'-(9-acridinylamino)-methanesulfone-m-anisidide) daunorubicin, and oxaunomycin (15, 16, 17). Not only aclarubicin, but also several other DNA binding agents such as ethidium bromide (24), 9-aminoacridines (7, 20), and chloroquine (18) can antagonize the cytotoxicity of topoisomerase II targeting agents. It is believed that these DNA binding drugs inhibit the initial DNA binding step of the enzyme and thereby suppress the interaction between the enzyme, the topoisomerase II targeting drug, and DNA. Recently, more specific interactions with topoisomerase II have been described. Thus, it appears that cation chelating bis-dioxypiperazines may lock topoisomerase II at its magnesium/ATP binding site at the stage of the catalytic cycle where the homodimeric enzyme is thought to be in the form of a closed bracelet surrounding the DNA (22, 23). By locking the enzyme, the bis-dioxopiperazine seems to hinder topoisomerase II poisons from exerting their cytotoxicity. Thus, the bis-dioxypiperazine derivative ICRF-187 (dexrazoxane; (+)-1,2-bis(3,5-dioxopiperazinyl-1-yl) propane) abolishes both DNA breaks and cytotoxicity caused by the topoisomerase II poisons etoposide and daunorubicin (25).

The antagonistic effect of ICRF-187 has been observed on the drug daunorubicin (14), but not on the chemically very similar doxorubicin, and this latter topoisomerase II poison is therefore excluded from the invention. Similarly no antagonism on clerocidin has been found.

SUMMARY OF THE INVENTION

The present invention provides an effective treatment of cancer by utilizing the antagonistic effect of a bis-dioxopiperazine on a topoisomerase II poison.

More specifically, the present invention relates to the treatment of malignant conditions which are sensitive to topoisomerase II poisons wherein the normal tissue is substantially protected from the poison by the bis-dioxopiperazine whereby the malignant conditions can be treated with higher dosages of the topoisomerase II poison.

In particular, the invention relates to a method for selectively killing tumour or metastatic cells within the central nervous system of a large mammal, such as a human. In the following description, the term patient may be used as a synonym for a large mammal.

The method comprises administration, e.g to a human, of an effective CNS-tumour- or metastasis-killing amount of a topoisomerase II poison except doxorubicin together with administration of a bis-dioxopiperazine compound. The non-CNS tissue of the patient is preferentially protected against the toxic action of the topoisomerase II poison by the bis-dioxypiperazine compound whereby increased dosages of the topoisomerase II poison are tolerated compared to the conventional administration of the topoisomerase II poison alone.

Topoisomerase II poisons such as etoposide are usually already used in maximally tolerated doses in the clinic, and therefore, dose increments which otherwise might have overcome drug resistance are not feasible. However, use of an antagonist together with an agonist according to the present invention may give new prospects. However, if such models of manipulation of etoposide effect are to be useful, they should enable significant dose escalations in vivo.

Here it is demonstrated that ICRF-187 in a mouse model markedly antagonizes the toxicity of etoposide in vivo and accordingly carries the prospect of powerful effect regulation.

Furthermore, it has surprisingly been found that when ICRF-187 is used with etoposide in vivo, the normal treatment schedule for etoposide relating to treatment every day in 3 days or in 5 days is not effective. Thus, the simultaneous use of ICRF-187 in the treatment with etoposide involves a completely new approach to the treatment schedule of topoisomerase II poisons.

m-AMSA 45 mg/kg m-AMSA 55 mg/kg

ICRF-187 125 mg/kg+m-AMSA 45 mg/kg

ICRF-187 125 mg/kg+m-AMSA 55 mg/kg

DETAILED DESCRIPTION OF THE PREFERRED EMBODIMENTS OF THE INVENTION

Figure 1:
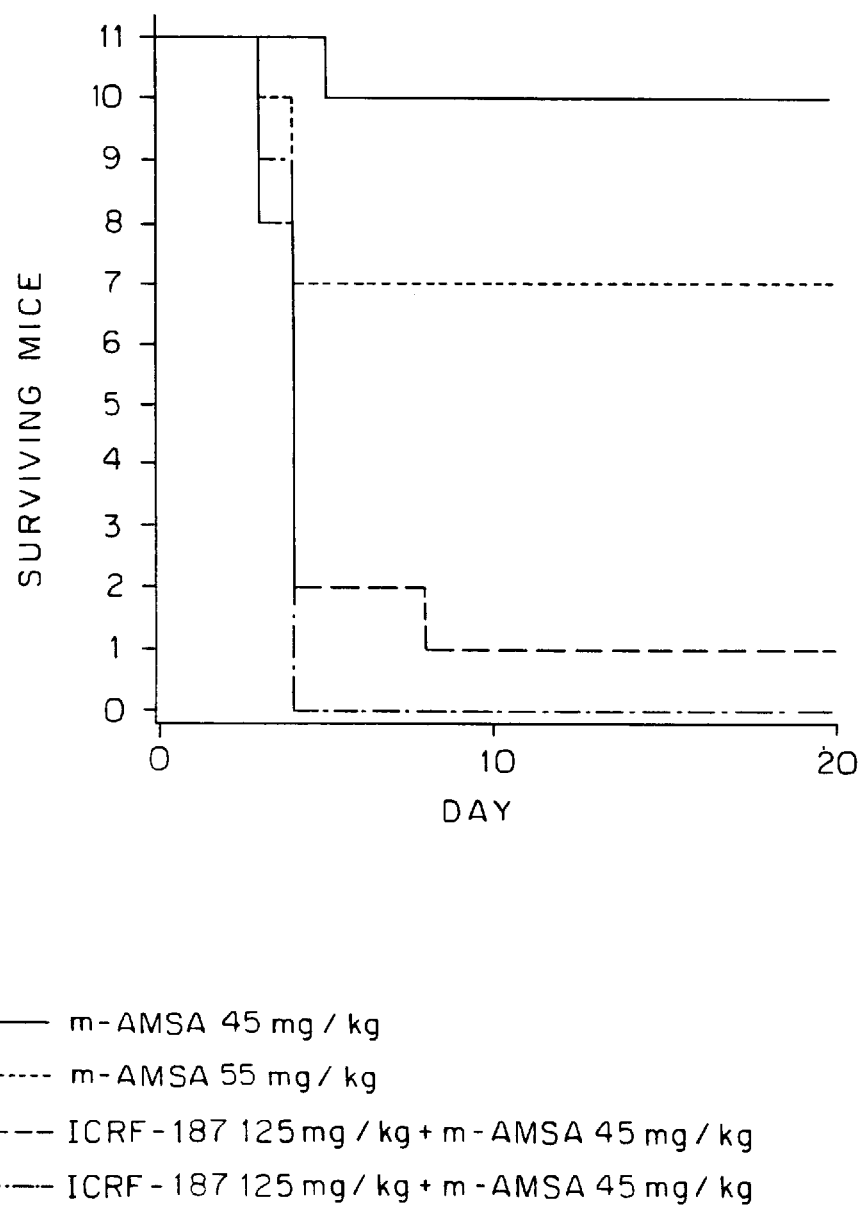
FIG. 1. shows the effect of ICRF-187 on the survival of mice treated with high-dose m-AMSA. Groups of 11 mice were treated as stated in the materials and methods section. Survival is increased in the two groups treated with the combination of drugs are compared to the groups treated with m-AMSA alone. No mice died after day 20.

Etoposide, VP-16, is a well known drug for use in the treatment of several cancers such as breast cancers, testicular cancers, small cell lung cancers, malignant lymphomas, and leukemias. These cancer forms are very often complicated with metastases to the CNS.

According to the present invention, topoisomerase II poisons are drugs such as the above-mentioned etoposide (VP-16), etoposide-phosphate, teniposide (VM-26) (has a potency which is about 10 fold more potent than VP-16), m-AMSA, daunorubicin, and mitoxantrone. Moreover, any topoisomerase II poison which inhibits the relegation step of the nuclear enzyme topoisomerase II at a step where the enzyme has created a cleavable complex in DNA is within the scope of the invention.

In the present context the term "conditions which are sensitive to topoisomerase II poisons" also includes any disease which would normally not be considered "sensitive" due to toxic side effects of the topoisomerase II poisons.

With respect to toxic side effect of the topoisomerase II poisons, the side effect weight loss has also been reduced by simultaneous treatment with ICRF-187. In this respect, the site of protection in vivo has been investigated in mice, and by organ histochemistry there appeared to be less toxicity in the gut by the method according to the present invention compared to treatment with the topoisomerase II poison alone. On the other hand, protection was surprisingly not observed with respect to leucocyte counts as leucopenia was observed in both cases.

According to the present invention, any ratio of the topoisomerase II poison and the bis-dioxopiperazine combination wherein an increased effect is observed compared to the administration of the topoisomerase alone may be used.

In practice, the side effect of VP-16 will be the limiting factor for the maximum dosage to be administered. It is contemplated that the effect of ICRF-187 shows a maximum in a range wherein the drug is relatively non-toxic and therefore VP-16 (etoposide) may be used in relatively high dosages compared to ICRF-187.

With respect to ICRF-187 it will be the side effect of the ICRF-187 which will determine the maximum dosage of this drug. However, it should be noted that in cancer treatment regimes, the cytotoxic treatment is often followed or accompanied by a second therapy for stimulation of the hemopoietic tissue, as myelosuppression such as leucopenia and thrombocytopenia is the side effect which normally limits the dosage of the cytostatic drugs which the patient can tolerate. Accordingly, very high dosages of topoisomerase II poison may be used according to the invention as in such instances the treatment may be performed together with a supporting therapy. In such high dosage treatment schedules, VP-16 may be used in dosages up to 10 g/m$^2$.

In the present context, equitoxic and equipotent dosages of topoisomerase II poisons are defined as dosages capable of inducing similar toxic effect or anticancer effect, respectively. By dosage is meant the total amount of drug which is administered in a single administration. Generally, cytotoxic drugs are administered as one daily dosage.

According to the present invention, the term large mammal relates in particular to humans. However, domestic animals, such as dogs, may be treated according to the present invention, if desired. Rodents are not within the scope of a large mammal.

In another aspect, the invention relates to a pharmaceutical kit for selectively killing tumour or metastatic cells within the central nervous system of a large mammal, in particular a human, comprising a dosage unit of a bis-dioxopiperazine and a pharmaceutically acceptable carrier and a dosage unit of topoisomerase II poisons except doxorubicin and a pharmaceutically acceptable carrier. The kit may further comprise the two dosage units in a single infusion system wherein the two dosage units are separated in two individual bags.

The dosage units may comprise the active ingredients as a dry substance, in concentrates suitable for dilution in accordance with the conventional formulation of the drugs, including tablet forms for the topoisomerase II poison.

In one embodiment, the kit comprises the two dosage units in separate containers, e.g. infusion bags which may be administered separately to the patient. In another embodiment, the two containers are connected, e.g by a Y-shaped tube, to a single infusion tube. Furthermore, additional containers, e.g. comprising neutral fluids, may be connected to the kit whereby the infusion tube may be flushed between the separate infusion of each of the drugs.

As mentioned above, etoposide is often used in a 3- to 5-day schedule in patients. However, when etoposide was used in a 5-day schedule in mice, the ICRF-187 mediated protection in vivo was not obtained. Protection was observed when etoposide was used once, once every five days, and once every week.

Comparison of different treatment schedules is shown in Table A from which it is clearly apparent that repeated treatments with the combination of the topoisomerase II poison and the bis-dioxypiperazine on day 1, day 3, and day 5 (every two days) result in considerable more deaths than the treatment on day 1, day 5 and day 9 (every four days) or on day 1, day 8, and day 15 (every seven days) even though a small tendency of protection by ICRF-187 is seen in the lower dosages of etoposide of 50 and 70 mg/kg.

Brief Discussion of the Results

The present study demonstrates that ICRF-187 antagonizes m-AMSA and etoposide mediated lethal toxicity in mice. Thus, ICRF-187 is an antidote which is effective against both intercalating and non-intercalating types of topoisomerase II poisons. This antagonism is marked as ICRF-187 enables a 3.6 fold increase in $LD_{10}$ of etoposide, i.e. a 3.6 fold increase in the dose which is killing 10% of the mice. Similar data have been obtained with teniposide resulting in a 3.4 fold increase in $LD_{10}$ of tenoposide. It is also remarkable that this protection was obtained within a large range of non-toxic ICRF-187 doses.

In vitro evidence suggests that this protection is related to an effect on topoisomerase II (22, 25, 27) and not to an inhibition of the formation of toxic free radicals by chelation of free iron. As ICRF-187 is a divalent cation chelator, a hypothesis would be that ICRF-187 interacts at the late magnesium/ATP binding stage of the enzyme's catalytic cycle where the homodimeric topoisomerase II is through to have the form of a closed bracelet surrounding the DNA. Roca et al. (22) recently performed in vitro studies demonstrating a bis-dioxypiperazine induced trapping of the enzyme in the form of a closed protein clamp. By reversible blocking at this stage, ICRF-187 is believed to be able to antagonize the religation inhibition invoked by topoisomerase II poisons.

However, it is not clear whether this marked in vivo protection of topoisomerase II poisons by ICRF-187 can be put to clinical use. Accordingly, the antitumour effect of equitoxic doses of etoposide and etoposide plus ICRF-187 was tested in mice bearing L1210 leukemia and a synergistic effect of the combination was found. From the knowledge of antagonism of etoposide cytotoxicity of tumour cells in clonogenic assay (25), no advantage of an i.p./i.p. co-treatment of an ascites tumour with ICRF-187 and etoposide would be expected. In accordance with this, the antitumour effect of equitoxic doses of etoposide and etoposide plus ICRF-187 was almost identical in mice with Ehrlich's ascites tumour cells which are basically confined to the peritoneal cavity (Table 5). In contrast, however, when L1210 cells were used which are known to metastasize readily (26), there was a trend towards a synergistic effect of the drug combination (Table 5). Finally a significant difference between etoposide alone and etoposide and protector was obtained when L1210 cells were inoculated into the cerebrum. Similar data have been obtained with Ehrlich's ascites tumour cells.

Although it is envisaged that an i.v. administration of the topoisomerase II poison and its antagonist ICRF-187 only has a clear effect when the tumour is situated within the CNS, the combination of the two drugs can be beneficial in other settings. Thus, ICRF-187 can protect systemically when the topoisomerase II poison is administered into a tumour containing a confined compartment. Such a compartment could be the peritoneal cavity or the pleural cavity, i.e. the ICRF-187 compound is administered i.v. whereas the topoisomerase II poison is administered locally. This approach can be useful e.g. in the treatment of mesothelioma or metastases from breast of lung cancer in the pleura or treatment of metastases of ovarian cancer and mammary cancer in the peritoneum. The optimum timing of such administrations can vary according to the specific compartment, the specific tumour and the topoisomerase poison.

In the conventional treatment schedules for cancer therapy, dosages to be received are calculated on the basis of the patients' surface area. Generally, the formula of Du Bois is used for calculation of the surface of an individual as follows: $=W^{0.425} \times H^{0.725} \times 0.007184$ wherein A=area (m$^2$), W=weight (kg) and H=height (cm).

The formula has been converted to a normogram wherein the relevant area can be read based on eight and height.

The corresponding dosages for a human and mice can be calculated according to the above, taken together with the conversion factor being so that 1 mg/kg in a large animal, such as a human of a height of 180 cm and weighing 70 kg corresponding to a surface area of about 1.87 m$^2$, corresponds to 3 mg/kg in a mouse.

It is believed that when used in the CNS the benefit of the method according to the present invention is an interaction of the antagonism of the drugs on the one hand and the pharmacological obstacle of the blood brain barrier on the other hand. Etoposide and its analogue teniposide pass the blood brain barrier (6), and the concentration of these drugs is especially high in CNS-metastases. In contrast, the concentration of the hydrophile ICRF-187 is very low in the cerebrospinal fluid (29); therefore, the combination of ICRF-187 and etoposide is especially of value in patients with etoposide sensitive brain tumours or metastases, as the combination would allow significant etoposide dose escalation by way of protection of normal tissues outside the CNS. In this context it is notable that etoposide is the most important single agent in the treatment of small cell lung cancer (SCLC), a disease which very often relapses in the CNS. This combination of drugs may be valuable in patients with SCLC and brain metastasis.

However, the principle of protection according to the present invention may be utilized in any other compartment of the body where the protecting bis-dioxypiperazine can be separated from a compartment where the tumour cells are present and where the cytotoxic drug is active.

It has been demonstrated that ICRF-187 is a non-toxic powerful protector of m-AMSA, daunorubicin, teniposide and etoposide toxicity in vivo allowing significant dose escalations. The etoposide dose increment made possible by treatment with ICRF-187 in non-toxic doses has surprisingly improved the effectiveness of treatment in mice inoculated intracranially with L1210 tumour cells. ICRF-187 therefore shows promise for increased tumour versus host selectivity.

In another aspect of the invention, the method relates to the treatment of a patient suffering from drug resistance towards a topoisomerase poison. Drug resistance is a condition wherein tumour cell killing cannot be obtained with dosages which have previously shown tumour killing effect.

DETAILED DISCLOSURE OF THE INVENTION

The bis-dioxopiperazine compounds, to which the present invention relates, are bis(3,5-dioxopiperazine-1-yl) alkanes having a structure as shown in the general formula I:

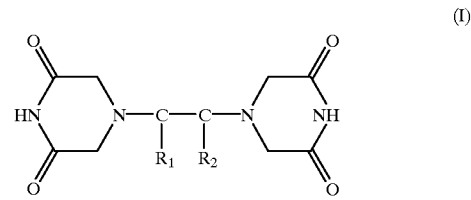

(I)

wherein R$^1$ is not the same as R$^2$ and R$^1$ and R$^2$ are hydrogen, or alkyl with 1–4 carbon atoms. The compounds may be in the (−) levo, (+) dextro or (±) racemic form. Preferably, R$^1$ is methyl and R$^2$ is hydrogen.

In a first aspect the present invention relates to a method for selectively killing tumour or metastatic cells within the central nervous system of a large mammal, in particular a human, comprising administering to a mammal an effective CNS-tumour- or metastasis-killing amount of a topoisomerase II poison except doxorubicin, and protecting non-CNS tissue of the mammal against the toxic action of the topoisomerase II poison by administration of a bis-dioxopiperazine compound, the topoisomerase II poison and the bis-dioxopiperazine compound being selected and administered, with respect to their amounts, expressed in mg per m$^2$ of the mammal and with respect to the ratio between their amounts, in such a manner that in mice, the corresponding amounts (the conversion factor being so that 1 mg/kg in a large animal, such as a human of a height of 180 cm and weighing 70 kg corresponding to a surface area of about 1.87 m$^2$, corresponds to 3 mg/kg in a mouse) will conform to the following criteria:

i) in mice inoculated into the cerebrum with 15×10$^4$ Ehrlich's ascites tumour cells or 10×10$^4$ L1210 leukemia cells in a volume of 30 µl of isotonic sodium chloride inoculated on day 0 into the temporal region, treatment i.p. on day 2 with the amount of the topoisomerase II poison and with simultaneous treatment with the amount of the bis-dioxopiperazine compound results in an increased life span of at least 125% compared to the increased life span in mice treated with topoisomerase II poison alone in an equitoxic dose (the equitoxic dose being calculated as the dose which in healthy mice results in a similar lethality as the combination); and ii) in mice treated with the topoisomerase II poison alone and combined with the bis-dioxopiperazine compound, respectively, the $LD_{10}$ of the combination is at least 25% higher than the $LD_{10}$ of the topoisomerase II poison alone.

In an additional aspect related to the above mentioned criterion i), the treatment with the amount of the bis-dioxypiperazine compound results in an increased life span of at least 150%, such as at least 200%, preferably at least 250%, such as about 300%, compared to the increased life span in mice treated with topoisomerase II poison alone in an equitoxic dose as defined above.

In a further aspect of the invention relates to the above mentioned criterion ii) in mice treated with the topoisomerase II poison alone and combined with the bis-dioxopiperazine compound, respectively, the $LD_{10}$ of the combination is at least 50% higher, such as at least 100% higher, preferably at least 150% higher, than the $LD_{10}$ of the topoisomerase II poison alone.

In a still further aspect of the invention related to the above mentioned criterion ii) in mice treated with the topoisomerase II poison alone and combined with the bis-dioxopiperazine compound, respectively, the $LD_{10}$ of the combination is at least 200% higher, even more preferred at least 250% higher, preferably at least 300% higher, more preferred at least 350% higher, such as 360% higher, than the $LD_{10}$ of the topoisomerase II poison alone.

In addition to criteria i) and ii) mentioned above, the method may further conform to the following criterion:

iii) in mice inoculated i.p. with $15 \times 10^6$ Ehrlich's ascites tumour cells on day 0, treatment i.p. on day 4 with the amount of the topoisomerase II poison and with simultaneous treatment with the amount of the bis-dioxopiperazine compound results in an increased life span of at the most 200%, such as at the most 150%, preferably at the most 125%, compared to the increased life span in mice treated with the topoisomerase II poison alone in an equitoxic dose (the equitoxic dose being defined above).

The interesting issue of criterion iii) above is that the model clearly indicates that the protecting effect of the tissue outside the CNS has a clear effect when the tumour is situated within the CNS. However, as the patient may suffer from a primary cancer outside the CNS, the treatment of the patient may be accomplished by conventional treatment of this cancer, e.g. by topoisomerase II poison in conventional dosages.

Generally, according to the present invention, the topoisomerase II poison is administered in a dosage amount equivalent to at least 200 mg/m² of etoposide, such as at least 500 mg/m² of etoposide, preferably at least 1000 mg/m² of etoposide, more preferably at least 1200 mg/m² of etoposide, even more preferred at least 1500 mg/m² of etoposide.

It will be obvious to the skilled person that the dosage may vary among the patients and also in the same patient, as the dosages may be calculated based on the patient's leucocyte count, platelet count and other factors relating to the hemopoietic status of the patient at the time of treatment.

Accordingly, in a further aspect of the invention the topoisomerase II poison is administered in a dosage amount equivalent to at least 2000 mg/m² of etoposide, such as at least 2500 mg/m² of etoposide, preferably at least 3000 mg/m² of etoposide, such as 3500 mg/m² of etoposide.

Such high dosages are indicated in patients who tolerate the topoisomerase II poison rather well, or because the bis-dioxopiperazine enables the dosages to be increased due to a superior protection of the combination outside the CNS. Cytotoxic drugs are generally rather well tolerated in the CNS compared to other tissues.

The bis-dioxopiperazine compound is preferably administered to the mammal in a dosage amount equivalent to at least 200 mg/m² of ICRF-187 such as at least 500 mg/m² of ICRF-187, preferably at least 1000 mg/m² of ICRF-187, more preferably at least 1200 mg/m² of ICRF-187, even more preferred at least 1500 mg/m² of ICRF-187.

The bis-dioxoypiperazine compounds according to the present invention are generally well tolerated by patients. Accordingly, if desired, the dosage may be increased. This will often be preferred in situations where a high dosage of topoisomerase poison II needs to be administered, e.g. in a schedule where single very high dosages are administered with long intervals.

Thus, in a further aspect of the invention the bis-dioxopiperazine compound is administered to the mammal in a dosage amount equivalent to at least 2000 mg/m² of ICRF-187, such as at least 2500 mg/m² of ICRF-187, preferably at least 3000 mg/m² of ICRF-187, such as 3500 mg/m² of ICRF-187.

As mentioned above, any ratio between the dosage amount of topoisomerase II poison and the dosage amount of the bis-dioxopiperazine which results in an increased survival compared to the equitoxic dosage of the topoisomerase II poison alone is within the scope of the invention. Nevertheless, it is believed that the best results will be obtained with ratios in the range of 1:6–6:1, such as 1:4–4:1, preferably in the range of 1:3–3:1, calculated on the weight of the active drugs. However, in the case of very potent drugs such as VP-26, the bis-dioxopiperazine may be used in relatively higher dosages than indicated with the above-mentioned ratios.

However, also in the situations where the most optimum ratio of the combination for a patient is not known, the ratio between the dosage amount of topoisomerase II poison and the dosage amount of the bis-dioxopiperazine to be administered is preferably in the range of 1:2–2:1, more preferably in the range of 1.5:2–2:1.5, the most preferred ratio being 1:1, calculated on the weight of the active drugs, as such ratios are believed to be sufficient in most cases.

In a special embodiment of the invention, the topoisomerase II poison is administered in a high dosage amount such as any dosage of between 3 and 10 g/m² or even up to 15 g/m². For many reasons, high dosages may be desirable, and up to the present invention, very high dosages would only be administered together with a supporting treatment such as stimulation of the hemopoietic tissue and/or followed by transplantation of hemopoietic tissue.

In a still further embodiment of the invention, the method may comprise additional therapy for stimulation of the hemopoietic tissue and/or transplantation of hemopoietic tissue.

In another embodiment of the invention, the mammal further receives a topoisomerase II poison alone and/or one or more other anticancer agents. This is especially the case when metastases of the CNS are treated.

The topoisomerase II poison and the bis-dioxopiperazine should be administered substantially simultaneously so that the protection of the tissue outside the CNS is present when the topoisomerase II poison exerts its cytotoxic effect.

Accordingly, in one aspect of the invention the bis-dioxopiperazine is administered prior to the administration of the topoisomerase II.

In a further aspect the bis-dioxopiperazine is administered in the period of from 72 hours before the administration of the topoisomerase II poison to 24 hours after, such as from 48 hours before to 12 hours after, more preferred from 24 hours before to 6 hours after, even more preferred from 12 hours before to 3 hours after, still more preferred from 6 hours before to 1 hour after, most preferred from 3 hours before to 1 hour after the administration of the topoisomerase II poison.

As the results indicate, it is believed that it may be an advantage to treat the patients with different intervals between the administration of the dosages than in the conventional schedules wherein the patient is treated every day for 3 or 5 days. Accordingly, in one embodiment the topoisomerase II poison is administered in a schedule where an administration is separated from the next administration by about 12 hours, such as by 2, 3, 4, 5, 6, or 7 days, although about 24 hours of separation may also be useful.

In another treatment according to the invention, each administration of the schedule is separated from the next administration by at least 2 days. Each administration may also be separated from the next administration by from about 3 days and up to about 3 weeks or even up to about 4 weeks if desired. One method according to the invention is a method wherein each administration is separated from the next administration by about 7 days.

According to the invention, administration of topoisomerase II poison except doxorubicin can be performed in various manners such as i.p.,i.v., or by local application, such as localized injection. Likewise, the administration of a bis-dioxopiperazine can be performed i.p. or i.v.

In one aspect the present invention relates to the use of a dosage unit of topoisomerase II poisons except doxorubicin and a dosage unit of a bis-dioxopiperazine together with a suitable pharmaceutical carrier for the preparation of a medicament for the treatment of malignant tumours of the CNS, including metastasis of the CNS of a mammal such as a human.

The present invention also relates to a pharmaceutical kit for selectively killing tumour or metastatic cells within the central nervous system of a large mammal, in particular a human, said kit comprising
   a) a dosage unit of a bis-dioxopiperazine, and a pharmaceutically acceptable carrier, and
   b) a dosage unit of topoisomerase II poisons except doxorubicin and a pharmaceutically acceptable carrier.

DESCRIPTION OF THE DRAWING

The abbreviations used are: m-AMSA: (4'-(9-acridinylamino)methanesulfone-m-anisidide, amsakrin). ICRF-187: (ADR-529, dexrazoxane, [(+)-1,2-bis(3,5-dioxopiperazinyl-1-yl)propane]).

ICRF-187 (Cardioxane™) purchased from EuroCetus B.V., Amsterdam, The Netherlands was dissolved in saline to 25 mg/ml. Etoposide (20 mg/ml) and paclitaxel (6 mg/ml) were bought from Bristol-Myers Squibb, Copenhagen, in solution for clinical use. m-AMSA purchased from Parke-Davis, Pontypool, Gwent, United Kingdom, was in N,N-dimethylacetamide solution and further diluted in acid lactose to 5 mg/ml.

In Vivo Experiments

First generation hybrids of female random bred Swiss mice and male inbred DBA (NDF1-hybrid) mice were used as previously described (5). The mice weighed between 19 and 21 g at the start of the experiments. Doses of etoposide, m-AMSA, and paclitaxel were adjusted according to weight and ICRF-187 was given in fixed doses either i.p. or i.v. in a tail vein 20 minutes before the investigated drug. Lethality was recorded and surviving mice were sacrificed after 60 days. Toxicity was evaluated by weight and leucocyte counts. For weight evaluations mice were treated with drugs, marked and weighed for eleven consecutive days. Blood for leucocyte counts was obtained from a tail vein and counted in a hemocytometer on days 3, 5 and 7 after treatment.

In therapy studies, mice were inoculated i.p. with either $10^5$ L1210 leukemia cells or $15 \times 10^6$ Ehrlich's ascites tumour cells on day 0 and treated with drugs i.p. on day 4 after inoculation. The brain tumour model consisted of $10^4$ L1210 cells or $15 \times 10^4$ Ehrlich's ascites tumour cells in a volume of 30 μl of isotonic sodium chloride inoculated on day 0 into the temporal region followed by treatment i.p. on day 2, 3 or 4 after inoculation.

Using the log probit method (4, 5, 14) the $LD_{90}$ (i.e. the dose killing 90% of the animals) of ICRF-187 in mice treated once i.p. was estimated to be 1500 mg/kg and the $LD_{10}$ to be 500 mg/kg. First the range of ICRF-187 doses capable of protecting against etoposide induced lethality was estimated. In drug combination studies, concentrations in the non-toxic 50 mg/kg to 250 mg/kg range were used except in one experiment, where 500 mg/kg was used. These varying doses were combined with a fixed dose of etoposide of 90 mg/kg. The results are shown in Table 1 and demonstrate that doses of ICRF-187 as low as 50 mg/kg provide good protection.

Next, the dose of etoposide was escalated up to 200 mg/kg and a fixed dose of ICRF-187 was used as protector of etoposide induced lethality. The results are shown in Table 2. ICRF-187 still provides significant protection at 140 mg of etoposide/kg, whereafter the ICRF-187 mediated protection decreases and is negligible at an etoposide dose of 180 mg/kg. $LD_{10}$ and $LD_{50}$ values (i.e. doses killing 10% and 50% of the animals, respectively) were computed using the maximum likelihood method on the compiled data (Table 3), showing that while the $LD_{10}$ of etoposide alone is 34 mg/kg it is 122 mg/kg when combined with 125 mg/kg ICRF-187, corresponding to a dose increment of etoposide of 360%. Similar results were obtained when ICRF-187 was given i.v. and etoposide i.p (data not shown). Thus, ICRF-187 is a powerful protector of etoposide induced lethality in mice. To test whether the ICRF-187 mediated antagonism translated to other topoisomerase II poisons in vivo, the toxicity of the combination of ICRF-187 and m-AMSA in healthy mice was investigated using the same schedule as described above. ICRF-187 protects not only against the non-intercalative etoposide, but also against death induced by the DNA intercalative topoisomerase II poison, m-AMSA. As the interaction between ICRF-187 and etoposide is considered to be on the target enzyme topoisomerase II, a non-topoisomerase II directed drug is not expected to be protected by ICRF-187. Therefore, the tubulin-directed drug paclitaxel (Taxol) in combination with ICRF-187 was not expected to be protected. As shown in Table 4 paclitaxel induced lethality cannot be antagonized by ICRF-187.

The effect of combining etoposide and ICRF-187 in mice inoculated i.p. with either Ehrlich's ascites tumour or L1210 tumour cells was then investigated. ICRF-187 had not antitumour effect, while etoposide at 33 mg/kg as expected demonstrated an increase in life span. In combination with ICRF-187 the dose of etoposide was escalated to 120 mg/kg and a non-significant increase in life span in three consecutive experiments using L1210 cells was observed while no synergy was found for Ehrlich's ascites tumour cells (Table 5).

The hypothesis that this difference in increase in life span could be caused by the metastatic potential of the L1210 leukemia cells and a possible difference in transport of the two drugs across the blood brain barrier was investigated. L1210 cells were therefore inoculated into the cerebrum and the animals treated i.p. As demonstrated in Table 6, a significant increase in life span using the high-dose etoposide schedule combined with ICRF-187 was obtained compared to etoposide alone.

The toxicity of drug combinations was evaluated in healthy mice by weight measurements. As shown in Table 7, the etoposide induced weight loss is largely prevented by ICRF-187.

TABLE A

Comparison of different treatment schedules

| Repeated treatments treatment day | 1, 3, and 5 (every two days) | 1, 5, and 9 (every four days) | 1, 8, and 15 (every seven days) |
|---|---|---|---|
| etoposide | | | |
| 50 mg/kg | 1/11 | 9/11 | 9/11 |
| 70 — | 0/11 | 2/11 | 0/11 |
| 90 — | 0/11 | 0/11 | 0/11 |
| etoposide + 100 mg/kg ICRF 187 | | | |
| 50 | 4/11 | 11/11 | 11/11 |
| 70 | 2/11 | 11/11 | 11/11 |
| 90 | 0/11 | 11/11 | 11/11 |
| ICRF-187 100 mg/kg | 11/11 | 11/11 | 11/11 |

(survivors/treated)

TABLE 1

Lethality of etoposide alone and combined with ICRF-187. The etoposide dose is fixed and the doses of ICRF-187 vary.

| Experiment # | Number of mice | VP-16 mg/kg | Survivors/ treated | ICRF-187 + VP-16 mg/kg | Survivors/ treated |
|---|---|---|---|---|---|
| # 1 | 11 | 90 | 1/11 (9%) | 50 + 90 | 11/11 (100%) |
| | | | | 125 + 90 | 11/11 (100%) |
| | | | | 250 + 90 | 11/11 (100%) |
| # 2 | 11 | 90 | 3/11 (27%) | 50 + 90 | 9/11 (82%) |
| | | | | 125 + 90 | 11/11 (100%) |
| | | | | 250 + 90 | 11/11 (100%) |
| # 3 | 11 | 90 | 5/11 (45%) | 250 + 90 | 11/11 (100%) |
| | | | | 500 + 90 | 11/11 (100%) |
| # 4 | 11 | 90 | 2/11 (18%) | 50 + 90 | 11/11 (100%) |
| | | | | 125 + 90 | 11/11 (100%) |
| | | | | 250 + 90 | 11/11 (100%) |

The lethality of etoposide is decreased by pretreatment with ICRF-187 in low, non-toxic doses. Drugs were given once i.p. ICRF-187 was given immediately before etoposide.

TABLE 2

Lethality of etoposide alone and combined with ICRF-187. The ICRF-187 dose is fixed and the doses of etoposide vary.

| Experiment # | Number of mice | VP-16 mg/kg | Survivors/ treated | ICRF-187 + VP-16 mg/kg | Survivors/ treated |
|---|---|---|---|---|---|
| # 1 | 11 | 90 | 8/11 (73%) | 125 + 90 | 11/11 (100%) |
| | | 100 | 2/11 (18%) | 125 + 100 | 11/11 (100%) |
| | | 120 | 1/11 (9%) | 125 + 120 | 11/11 (100%) |
| | | 140 | 0/11 (0%) | 125 + 140 | 11/11 (100%) |
| # 2 | 11 | 90 | 3/11 (27%) | 125 + 90 | 11/11 (100%) |
| | | 100 | 2/11 (18%) | 125 + 100 | 10/11 (91%) |
| | | 120 | 0/11 (0%) | 125 + 120 | 8/11 (73%) |
| | | 140 | 1/11 (9%) | 125 + 140 | 6/11 (55%) |
| # 3 | 11 | 90 | 8/11 (73%) | 125 + 90 | 11/11 (100%) |
| | | 100 | 3/11 (27%) | 125 + 100 | 11/11 (100%) |
| | | 120 | 1/11 (9%) | 125 + 120 | 11/11 (100%) |
| | | 140 | 2/11 (18%) | 125 + 140 | 9/11 (82%) |
| # 4 | 11 | 90 | 3/11 (27%) | 125 + 90 | 9/11 (82%) |
| | | 140 | 1/11 (9%) | 125 + 140 | 9/11 (82%) |
| | | 180 | 0/11 (0%) | 125 + 180 | 1/11 (9%) |
| | | 200 | 0/11 0% | 125 + 200 | 0/11 0% |
| # 5 | 11 | 90 | 3/11 (27%) | 125 + 90 | 11/11 (100%) |
| | | 140 | 4/11 (36%) | 125 + 140 | 11/11 (100%) |
| | | 180 | 0/11 (0%) | 125 + 180 | 5/11 (45%) |
| | | 200 | 2/11 (18%) | 125 + 200 | 2/11 (18%) |
| # 6 | 11 | 90 | 1/11 (9%) | 125 + 90 | 11/11 (100%) |
| | | 140 | 0/11 (0%) | 125 + 140 | 8/11 (73%) |
| | | 180 | 2/11 (18%) | 125 + 180 | 5/11 (45%) |
| | | 200 | 1/11 (9%) | 125 + 200 | 2/11 (18%) |

In etoposide dose escalation experiments ICRF-187 still provides significant protection at 140 mg of etoposide/kg.

TABLE 3

Estimation of $LD_{10}$ and of $LD_{50}$

| | log $LD_{10}$ | SE | $LD_{10}$ mg/kg | log $LD_{50}$ | SE | $LD_{50}$ mg/kg |
|---|---|---|---|---|---|---|
| VP-16 | 1.531 | 0.123 | 34.0 | 1.853 | 0.051 | 71.3 |
| ICRF + VP-16 | 2.088 | 0.009 | 122.4 | 2.214 | 0.011 | 163.8 |

Calculation of $LD_{10}$ and $LD_{50}$ using the maximum likelihood estimation. The 6 experiments in Table 2 are included in the computations.

TABLE 4

Lethality of paclitaxel alone and combined with ICRF-187.

| Paclitaxel mg/kg | Survivors/treated | % | Paclitaxel + ICRF-187 mg/kg | Survivors/treated | % |
|---|---|---|---|---|---|
| 30 | 22/22 | 100 | 125 + 30 | 22/22 | 100 |
| 40 | 12/22 | 55 | 125 + 40 | 11/22 | 50 |
| 50 | 0/22 | 0 | 125 + 50 | 2/22 | 9 |

The compiled data from two experiments showing that paclitaxel induced lethality cannot be protected by pretreatment with ICRF-187. Groups of 11 mice were treated once i.p. with or without pretreatment with ICRF-187.

TABLE 5

Treatment with etoposide and ICRF-187 in tumour bearing mice

| Ehrlich's tumour cells | | | | L1210 tumour cells | | | |
|---|---|---|---|---|---|---|---|
| Etoposide Dose (mg/kg) 33 | Etoposide + ICRF-187 Dose (mg/kg) 120 + 125 | | | Etoposide Dose (mg/kg) 33 | Etoposide + ICRF-187 Dose (mg/kg) 120 + 125 | | |
| N | ILS (%) | ILS (%) | p | N | ILS (%) | ILS (%) | p |
| 11 | 53 | 64 | NS | 22 | 113 | 131 | NS |
| 11 | 40 | 43 | NS | 22 | 100 | 138 | NS |
| 11 | 35 | 36 | NS | 20 | 88 | 219 | <0.01 |

Calculated values of $LD_{10}$ for etoposide alone (33 mg/kg) and for etoposide in combination with ICRF-187 (120 mg/kg) were used for treatment studies. $1 \times 10^5$ L1210 tumour cells or $15 \times 10^6$ Ehrlich's ascites tumour cells were inoculated i.p. on day 0 and mice were treated i.p. on day 4. The Mann Whitney test was used for statistical evaluation.

TABLE 5A

Calculations on the results from the treatment on mice bearing Ehrlich's tumour cells as shown in Table 5

| Ehrlich's tumour cells | | | | Ehrlich's tumour cells increased life span | | |
|---|---|---|---|---|---|---|
| Etoposide Dose (mg/kg) 33 | Etoposide + ICRF-187 Dose (mg/kg) 120 + 125 | | Etoposide Dose (mg/kg) 33 | Etoposide + ICRF-187 Dose (mg/kg) 120 + 125 | | |
| | | | | increase in | | |
| N | ILS (%) | ILS (%) | p | ILS (%) | ILS (%) | ILS (%) |
| 11 | 53 | 64 | NS | 100 | 21 | 121 |
| 11 | 40 | 43 | NS | 100 | 8 | 108 |
| 11 | 35 | 36 | NS | 100 | 3 | 103 |

TABLE 5B

Calculations on the results from the treatment on mice bearing L 1210 tumour cells as shown in Table 5

| L 1210 tumour cells | | | | L 1210 tumour cells increased life span | | |
|---|---|---|---|---|---|---|
| Etoposide Dose (mg/kg) 33 | Etoposide + ICRF-187 Dose (mg/kg) 120 + 125 | | Etoposide Dose (mg/kg) 33 | Etoposide + ICRF-187 Dose (mg/kg) 120 + 125 | | |
| | | | | increase in | | |
| N | ILS (%) | ILS (%) | p | ILS (%) | ILS (%) | ILS (%) |
| 11 | 113 | 131 | NS | 100 | 16 | 116 |
| 11 | 100 | 138 | NS | 100 | 38 | 138 |
| 11 | 88 | 219 | <0.01 | 100 | 149 | 249 |

TABLE 6

Treatment of mice inoculated i.c. with $10^4$ L1210 tumour cells.

L1210 tumour cells inoculated into the cerebrum

| Etoposide Dose (mg/kg) 33 | Etoposide + ICRF-187 Dose (mg/kg) 120 + 125 | | |
|---|---|---|---|
| N | ILS (%) | ILS (%) | p |
| 18 | 13 | 38 | <0.01 |
| 18 | 21 | 38 | <0.01 |
| 18 | 13 | 63 | <0.01 |

Groups of 18 mice were inoculated on day 0 and treated on day 2. The Mann-Whitney test was used for statistical evaluation.

TABLE 6A

Treatment of mice inoculated i.c. with $15 \times 10^5$ Ehrlich's ascites tumour cells.

Ehrlich's ascites tumour cells inoculated into the cerebrum

| Etoposide Dose (mg/kg) 33 | Etoposide + ICRF-187 Dose (mg/kg) 120 + 125 | | |
|---|---|---|---|
| N | ILS (%) | ILS (%) | p |
| 9 | 11 | 33 | NS |

Groups of 9 mice were inoculated on day 0 and treated on day 2. The Mann-Whitney test was used for statistical evaluation. The results in Table 6A show an increased life span from 11% to 33% corresponding to 300% compared to the increased life span in mice treated with topoisomerase II poison alone in an equitoxic dose.

TABLE 7

Weight at nadir (median and range in grams)

| Control | 21.4 [20.4–21.8] |
|---|---|
| ICRF-187 125 mg/kg | 21.2 [19.7–22.2] |
| Etoposide | 15.4 [15.2–21.4] |

TABLE 7-continued

Weight at nadir (median and range in grams)

| | |
|---|---|
| 90 mg/kg ICRF-187 + Etoposide 125 mg/kg + 90 mg/kg | 19.9 [18.0–20.8] |

Groups of 5 mice were treated with drugs as stated and weighed for 11 consecutive days. Etoposide alone caused a median 6 g decrease in body weight, whereas the combination of drugs only resulted in a weight loss of 1.5 g.

CLINICAL TRIAL

The following clinical test is performed:
1. Purpose
  1. To determine the maximum tolerable dose (MTD) of etoposide in combination with a constant dose of ICRF-187 given once a week.
  2. To evaluate the toxicity/tolerability of the combination treatment.
  3. To evaluate the response rate of this treatment in patients having a histologically verified lung cancer and brain metastases verified by CT scanning.
2. Treatment Doses and Duration Dose escalation scheme

| Escalation number | ICRF-187 mg/m² | Etoposide mg/m² |
|---|---|---|
| 1 | 1500 | 500 |
| 2 | 1500 | 1000 |
| 3 | 1500 | 1200 |
| 4 | 1500 | 1500 |
| 5 | 1500 | 2000 |
| 6 | 1500 | 2500 |
| 7 | 1500 | 3000 |

These doses are given once a week during hospitalization until progressive disease or pronounced toxicity [grade IV common toxicity criteria (CTC)]. One treatment series is constituted by weekly treatments during four consecutive weeks. After one series, the effect on tumour formation is evaluated. Then the weekly treatments are continued and the response evaluated every four weeks. The treatment is carried out in a total of 3 series, i.e. 12 treatments. One patient is included at the first dose level; after this unexpected haematological and non-haematological side effects are awaited for one week. Two more patients are included at the same dose level. If, at this dose level, there is no grade II CTC toxicity, the dose is escalated to the next dose level. If one out of three patients shows grade II CTC toxicity, three more patients are included at the level in question. If two out of these six patients show grade II CTC toxicity, MTD has been reached and the dose is reduced to ⅔ of the used escalation step. At the MTD thus determined, patients are included so that there are 12 patients in total at the level in question. The treatment is postponed for at the most 3 weeks in the case of non-restoration. No dose escalation is to be made with respect to the individual patient. The ICRF-187 dose has been selected so as to obtain a ratio of 1:1 between the substances.
3. Analysis Criteria
3.a. Response The ideal thing is that all measurable lesions are measured at each evaluation. If multiple lesions are found, this may not be possible, and under such circumstances up to 8 representative lesions must be selected.

Measurable Disease (Measurable Uni- or Bidimensionally)
1. Complete response (CR): Disappearance of all known disease, determined by two observations at intervals of at least 4 weeks.
2. Partial response (PR): In case of bidimensionally measurable disease, a reduction of at least 50% of the sum of the product of the largest perpendicular diameters of all measurable lesions, determined by two observations at intervals of at least 4 weeks. In case of unidimensionally measurable disease, a reduction of at least 50% of the sum of the largest diameters of all lesions, determined by two observations at intervals of at least 4 weeks.
3. No-change disease (NC): In case of bidimensionally measurable disease, a <50% reduction and a <25% increase of the sum of the product of the largest perpendicular diameters of all measurable lesions. In case of unidimensionally measurable disease, a <50% reduction and a <25% increase of the sum of the diameter of all lesions. No new lesions must arise.
4. Progressive disease (PD): A >25% increase of the size of at least one bidimensionally or unidimensionally measurable lesion or appearance of a new lesion.

REFERENCES

2. Bork E, Ersbøll J, Dombernowsky P, Bergman B, Hansen M, Hansen H H (1991) Teniposide and etoposide in previously untreated small-cell lung cancer: A randomized study. J Clin Oncol, 9: 1627.
4. Cornfield J, Mantel N (1950) Some new aspects of the application of maximum likelihood to the calculation of the dosage response curve. Amer Statis Ass J. p. 181.
5. Danø K (1971) Development of resistance to daunomycin (NSC-82151) in Ehrlich's ascites tumour. Cancer Chemother Rep. 55: 133.
6. Donelli M G, Zucchetti M, D'Incalci M (1992) Do anticancer agents reach the tumour target in the human brain? Cancer Chemother Pharmacol. 30: 351.
7. Finlay G F, Wilson W R, Baguley B C (1989) Chemoprotection by 9-aminoacridine derivatives against the cytotoxicity of topoisomerase II-directed drugs. Eur J Cancer Clin Oncol. 25: 1695.
12. Herman E H, Witiak D T, Hellmann K, Waravdekar V S (1982) Biological properties of ICRF-159 and related bis(dioxopiperazine) compounds. Adv Pharmacol Chemother 19: 249.
13. Holm B, Jensen P B, Sehested M, Hansen H H (1994) In vivo inhibition of etoposide (VP-16) mediated apoptosis, toxicity, and antitumour effect by the topoisomerase II uncoupling anthracycline aclarubicin. Cancer Chemother Pharmacol. 34: 503.
14. Jensen P B, Roed H, Skovsgaard T, Friche E, Vindeløv L L, Hansen H H, Spang-Thomsen M (1990) Antitumour activity of the two epipodophyllotoxin derivatives VP-16 and VM-26 in preclinical systems: A comparison of in vitro and in vivo drug evaluation. Cancer Chemther Pharmacol. 27: 194.
15. Jensen P B, Sørensen B S, Demant E J F, Sehested M, Jensen P S, Vindeløv L, Hansen H H (1991) Antagonistic effect of aclarubicin on the cytotoxicity of etoposide and 4'-(9-acridinylamino)methanesulfon-m-anisidide in human small cell lung cancer cell lines and on topoisomerase II-mediated DNA cleavage. Cancer Res. 51: 3311.

16. Jensen P B, Jensen P S, Demant E J F, Friche E, Sørensen B S, Sehested M, Wassermann K, Vindeløv L, Westergaard O, Hansen H H (1991) Antagonistic effect of aclarubicin on daunorubicin-induced cytotoxicity inhuman small cell lung cancer cells: Relationship to DNA integrity and topoisomerase II. Cancer Res. 51: 5093.

17. Jensen P B, Sørensen B S, Sehested M, Demant E J F, Kjeldsen E, Friche E, Hansen H H (1993) Different modes of anthracycline interaction with topoisomerase II. Separate structures critical for DNA-cleavage, and for overcoming topoisomerase II-related drug resistance. Biochem Pharmacol. 45: 2025.

18. Jensen P B, Sørensen B S, Sehested M, Grue P, Demant E J F, Hansen H H (1994) Targeting the cytotoxicity of topoisomerase II-directed epipodophyllotoxins to tumour cells in acidic environments. Cancer Res. 54: 2959.

19. Liu L F (1989) DNA topoisomerase poisons as antitumour drugs. Annu Rev Biochem. 58: 351.

20. Pommier Y, Covey J, Kerrigan D, Mattes W, Markovits J, Kohn K W (1987) Role of DNA intercalation in the inhibition of purified mouse leukemia (L1210) DNA topoisomerase II by 9-aminoacridines. Biochem Pharmacol. 36: 3477.

21. Pommier Y, Kohn K (1989) Topoisomerase II inhibition by antitumour intercalators and demethylepipodophyllotoxins. In: R I Glazer (ed) Development in Cancer Chemotherapy. Boca Raton, Fla.: CRC Press Inc. p 175.

22. Roca J, Ishida R, Berger J M, Andoh T, Wang J C (1994) Antitumour bis-dioxopiperazines inhibit yeast DNA topoisomerase II by trapping the enzyme in the form of a closed protein clamp. Proc Natl Acad Sci USA, 91: 1781.

23. Roca J, Wang J C (1994) DNA transport by a type II DNA topoisomerase: Evidence in favor of a two-gate mechanism. Cell, 77: 609.

24. Rowe T, Kupfer G, Ross W (1985) Inhibition of epipodophyllotoxin cytotoxicity by interference with topoisomerase-mediated DNA-cleavage. Biochem Pharmacol. 34: 2483.

25. Sehested M, Jensen P B, Sørensen B S, Holm B, Friche E, Demant E J F (1993) Antagonistic effect of the cardioprotector (+)-1,2-bis(3,5-dioxopiperazinyl-1-yl) propane (ICRF-187) on DNA breaks and cytotoxicity induced by the topoisomerase II directed drugs daunorubicin and etoposide (VP-16). Biochem Pharmacol. 46: 389.

26. Skipper H E, Schabel Jr F M, Wilcox W S (1964) Experimental evaluation of potential anticancer agents. XIII. On the criteria and kinetics associated with "curability" of experimental leukemia. Cancer Chemother Rep. 35: 1.

27. Tanabe K, Ikegami Y, Ishida R, Andoh T (1991) Inhibition of topoisomerase II by antitumour agents bis(2,6-dioxopiperazine derivatives. Cancer Res. 51: 4903.

28. Tewey K M, Rowe T C, Yang L, Halligan B D, Liu L F (1984) Adriamycin-induced DNA damage mediated by mammalian DNA topoisomerase II. Science 226: 466.

29. Von Hoff D D, Soares N, Gormley P, Poplack D G (1980) Pharmacokinetics of ICRF-187 in the cerebrospinal fluid of subhuman primates. Cancer Treat Rep. 64: 734.

What is claimed is:

1. A method for selectively killing tumour cells within the central nervous system (CNS) compartment of a human, comprising administering to a human, outside said compartment, an effective tumour-cell killing amount of a topoisomerase II poison except doxorubicin, and protecting non-tumourous tissue outside said compartment of a human against the toxic action of the topoisomerase II poison by administration outside said compartment of a topoisomerase II poison-protective amount of a bis-dioxopiperazine compound, said topoisomerase II poison being antagonized by said bis-dioxopiperazine compound, and said compartment being one where the topoisomerase II poison is active and which is substantially inaccessible, as a result of the blood-brain barrier, to said bis-dioxopiperazine as administered, but accessible to said topoisomerase II poison as administered, where said topoisomerase II poison is etoposide or teniposide and where said bis-dioxopiperazine is (+)-1,2-bis(3,5-dioxopiperazinyl-1-yl)propane (ICRF-187) or its (−)-isomer, where said combination of administrations is pharmaceutically acceptable with the proviso that the tumour cell is not in a host infected with HIV.

2. A method according to claim 1 for selectively killing tumour or metastatic cells within the central nervous system of a human, comprising administering to a human an effective CNS-tumour- or metastasis-killing amount of a topoisomerase II poison except doxorubicin, and protecting non-CNS tissue of a human against the toxic action of the topoisomerase II poison by administration of a bis-dioxopiperazine compound, the topoisomerase II poison and the bis-dioxopiperazine compound being selected and administered, with respect to their amounts, expressed in mg per m$^2$ of a human and with respect to the ratio between their amounts, in such a manner that in mice, the corresponding amounts (the conversion factor being so that 1 mg/kg in a human of a height of 180 cm and weighing 70 kg corresponding to a surface area of about 1.87 m$^2$, corresponds to 3 mg/kg in a mouse) will conform to the following criteria:

i) in mice inoculated into the cerebrum with 15×10$^4$ Ehrlich's ascites tumour cells or 10×10$^4$ L1210 leukaemia cells in a volume of 30 µl of isotonic sodium chloride inoculated on day 0 into the temporal region, treatment i.p. on day 2 with the amount of the topoisomerase II poison and with simultaneous treatment with the amount of the bis-dioxopiperazine compound results in an increased life span of at least 125% compared to the increased life span in mice treated with topoisomerase II poison alone in an equitoxic dose (the equitoxic dose being calculated as the dose which in healthy mice results in a similar lethality as the combination); and/or ii) in mice treated with the topoisomerase II poison alone and combined with the bis-dioxopiperazine compound respectively, the LD$_{10}$ of the combination is at least 25% higher than the LD$_{10}$ of the topoisomerase II poison alone.

3. A method for selectively killing tumour or metastatic cells within the intraperitoneal cavity or intrapleural cavity of a human, comprising administering to a human an effective tumour- or metastasis-killing amount of a topoisomerase II poison except doxorubicin and daunorubicin, and protecting non-tumourous tissue of a human against the toxic action of the topoisomerase II poison by administration of a bis-dioxopiperazine compound, the administration of topoisomerase II poison being performed locally to the cavity while the bis-dioxopiperazine compound is being administered systemically.

4. A method according to claim 1 wherein the topoisomerase II poison and the bis-dioxopiperazine compound are selected and administered to further conform to the following criterion:

iii) in mice inoculated i.p. with $15 \times 10^6$ Ehrlich's ascites tumour cells on day 0, treatment i.p. on day 4 with the amount of the topoisomerase II poison and with simultaneous treatment with the amount of the bis-dioxopiperazine compound results in an increased life span of at the most 200%, compared to the increased life span in mice treated with the topoisomerase II poison alone in an equitoxic dose (the equitoxic dose being defined as in claim 2).

5. A method according to claim 1, wherein the topoisomerase II poison is administered in a dosage amount equivalent to at least 200 mg/m² of etoposide.

6. A method according to claim 1, wherein the topoisomerase II poison is administered in a dosage amount equivalent to at least 2000 mg/m² of etoposide.

7. A method according to claim 1, wherein the bis-dioxopiperazine compound is administered to a human in a dosage amount equivalent to at least 200 mg/m² of ICRF-187.

8. A method according to claim 1, wherein the bis-dioxopiperazine compound is administered to a human in a dosage amount equivalent of at least 2000 mg/m² of ICRF-187.

9. A method according to claim 1, wherein the ratio between the dosage amount of topoisomerase II poison and the dosage amount of the bis-dioxopiperazine to be administered is in the range of 1:6–6:1.

10. A method according to claim 1, wherein the ratio between the dosage amount of topoisomerase II poison and the dosage amount of the bis-dioxypiperazine to be administered is in the range of 1:2–2:1, calculated on the weight of the active drugs.

11. A method according to claim 1, wherein the topoisomerase II poison is administered in a dosage of between 3 and 15 g/m².

12. A pharmaceutical kit comprising
a dosage unit of (a) a bis-dioxopiperazine and a pharmaceutically acceptable carrier, and
a dosage unit of (b) topoisomerase II poisons except doxorubicin and a pharmaceutically acceptable carrier, said (a) and (b) being provided in amounts effective, in combination, for selectively killing tumor or metastatic cells where said topoisomerase II poison is etoposide or teniposide and where said bis-dioxopiperazine is (+)-1,2-bis(3,5-dioxopiperazinyl-1-yl)propane (ICRF-187) or its (−)isomer.

13. A method according to claim 1, wherein the topoisomerase II poison and the bis-dioxopiperazine are administered simultaneously.

14. A method according to claim 1, wherein the bis-dioxopiperazine is administered prior to the administration of the topoisomerase II.

15. A method according to claim 14, wherein the bis-dioxopiperazine is administered in the period of from 72 hours before the administration of the topoisomerase II poison to 24 hours after.

16. A method according to claim 1, wherein the topoisomerase II poison and the bis-dioxopiperazine compound are selected and administered to conform to the following criterion:

i) in mice inoculated into the cerebrum with $15 \times 10^4$ Ehrlich's ascites tumour cells in a volume of 30 μl of isotonic sodium chloride inoculated on day 0 into the temporal region, treatment i.p. on day 2 with the amount of the topoisomerase II poison and with simultaneous treatment with the amount of the bis-dioxopiperazine compound results in an increased life span of at least 150%, compared to the increased life span in mice treated with topoisomerase II poison alone in an equitoxic dose as defined in claim 2.

17. A method according to claim 1, wherein the topoisomerase II poison and the bis-dioxopiperazine compound are selected and administered to conform to the following criterion:

ii) in mice treated with the topoisomerase II poison alone and combined with the bis-dioxopiperazine compound, respectively, the $LD_{10}$ of the combination is at least 50% higher than the $LD_{10}$ of the topoisomerase II poison alone.

18. A method according claim 1, wherein the topoisomerase II poison and the bis-dioxopiperazine compound are selected and administered to conform to the following criterion:

iia) in mice treated with the topoisomerase II poison alone and combined with the bis-dioxopiperazine compound respectively, the $LD_{10}$ of the combination is at least 200% higher than the $LD_{10}$ of the topoisomerase II poison alone.

19. A method according to claim 1, wherein the topoisomerase II poison is administered in a schedule where an administration is separated from the next administration by at least 2 days (48 hours).

20. A method according to claim 1, wherein the topoisomerase II poison is administered in a schedule where an administration is separated from the next administration by at least 4 days.

21. A method according to claim 1, wherein the topoisomerase II poison is administered in a schedule where each administration is separated from the next administration by at least 12 hours.

22. A method according to claim 21, wherein each administration is separated from the next administration by from about 3 days to about 3 weeks.

23. A method according to claim 22, wherein each administration is separated from the next administration by about 7 days.

24. A method according to claim 1, wherein the topoisomerase II poison is etoposide.

25. A method according to claim 1, wherein the topoisomerase II poison is teniposide (VM-26).

26. A method according to claim 1, wherein the topoisomerase II poison is etoposide-phosphate.

27. The method of claim 1 in which the amount of the topoisomerase II poison administered is larger and more effective than the dose which would be an equitoxic dose in the absence of said bis-dioxopiperazine.

28. The method of claim 2 in which the amount of the topoisomerase II poison administered is larger and more effective than the dose which would be an equitoxic dose in the absence of said bis-dioxopiperazine.

29. The method of claim 1 in which the compartment is the peritoneal cavity.

30. The method of claim 1 in which the compartment is the pleural cavity.

31. The method of claim 1 where the poison and the compound are administered by infusion.

32. The method of claim 1 where the poison and the compound are administered intravenously.

33. The method of claim 1 where the poison and the compound are administered intraperitoneally.

34. The method of claim 1 in which the amount of the topoisomerase II poison administered is higher than what would be a pharmaceutically acceptable amount in the absence of the administration of said bis-dioxopiperazine.

35. The method of claim 1 in which the tumor cells belong to a primary cancer of the CNS.

36. The method of claim 1 in which the tumor cells belong to a CNS metastasis of a primary cancer located outside the CNS.

37. The method of claim 36 in which the metastasized cancer is a breast cancer.

38. The method of claim 36 in which the metastasized cancer is a testicular cancer.

39. The method of claim 36 in which the metastasized cancer is a small lung cancer.

40. The method of claim 36 in which the metastasized cancer is a lymphoma.

41. The method of claim 36 in which the metastasized cancer is a leukemia.

42. The method of claim 1 in which the amount of the bis-dioxopiperazine administered is such that if administered alone it would not have a statistically significant antitumor effect.

43. A method for selectively killing tumor cells in the peritoneal cavity compartment of a human, comprising administering to said human, into said compartment, a tumor killing-amount of a topoisomerase II poison, said poison being etoposide or teniposide, and administering to said human, outside said compartment, a topoisomerase II poison-antagonizing amount of a bis-dioxopiperazine compound, said compound being (+)-1,2-bis(3,5-dioxopiperazinyl-1-yl)propane or its (−)isomer, thereby protecting nontumor tissue outside said compartment from said topoisomerase II poison, where said combination of administrations is pharmaceutically acceptable with the proviso that the tumour cell is not in a host infected with HIV.

44. The method of claim 43 wherein the tumor cells are peritoneal metastases of an ovarian cancer or a mammary cancer.

45. The method of claim 1 in which both the topoisomerase II poison and the bis-dioxopiperazine are administered intravenously.

46. A method according to claim 1, wherein the ratio between the dosage amount of topoisomerase II poison and the dosage amount of the bis-dioxopiperazine to be administered is in the range of 1.5:2–2:1.5 calculated on the weight of the active drugs.

47. A method according to claim 14, wherein the bis-dioxopiperazine is administered in the period from 48 hours before to 12 hours after administration of the topoisomerase II poison.

48. A method according to claim 14, wherein the bis-dioxopiperazine is administered in the period from 24 hours before to 6 hours after administration of the topoisomerase II poison.

49. A method according to claim 14, wherein the bis-dioxopiperazine is administered in the period from 12 hours before to 3 hours after administration of the topoisomerase II poison.

50. A method according to claim 14, wherein the bis-dioxopiperazine is administered in the period from 6 hours before to 1 hour after administration of the topoisomerase II poison.

51. A method according to claim 14, wherein the bis-dioxopiperazine is administered in the period from 3 hours before to 1 hour after administration of the topoisomerase II poison.

52. A method according to claim 1, wherein the topoisomerase II poison and the bis-dioxopiperazine are administered simultaneously.

53. A method according to claim 1 in which said topoisomerase II poison and said bis-dioxopiperazine are administered in a plurality of administrations.

54. The method of claim 53 in which the interval between administrations of the poison and the interval between administrations of the bis-dioxopiperazine are each four days.

* * * * *